United States Patent
Nguyen et al.

(10) Patent No.: US 12,181,799 B2
(45) Date of Patent: Dec. 31, 2024

(54) RESIST COMPOSITIONS AND SEMICONDUCTOR FABRICATION METHODS USING THE SAME

(71) Applicant: Samsung Electronics Co., Ltd., Suwon-si (KR)

(72) Inventors: Thanh Cuong Nguyen, Hwaseong-si (KR); Daekeon Kim, Hwaseong-si (KR); Tsunehiro Nishi, Seongnam-si (KR); Naoto Umezawa, Seongnam-si (KR); Hyunwoo Kim, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 889 days.

(21) Appl. No.: 16/947,515

(22) Filed: Aug. 5, 2020

(65) Prior Publication Data

US 2021/0181628 A1  Jun. 17, 2021

(30) Foreign Application Priority Data

Dec. 17, 2019  (KR) .................. 10-2019-0168997

(51) Int. Cl.
| G03F 7/004 | (2006.01) |
| C07C 25/13 | (2006.01) |
| G03F 7/038 | (2006.01) |
| G03F 7/039 | (2006.01) |
| H01L 21/027 | (2006.01) |

(52) U.S. Cl.
CPC ............ G03F 7/0045 (2013.01); C07C 25/13 (2013.01); G03F 7/038 (2013.01); G03F 7/039 (2013.01); H01L 21/0274 (2013.01)

(58) Field of Classification Search
CPC ........ G03F 7/0045; G03F 7/038; G03F 7/039; C07C 25/13
See application file for complete search history.

(56) References Cited

U.S. PATENT DOCUMENTS

| 6,258,507 B1 * | 7/2001 | Ochiai ................. G03F 7/039 430/326 |
| 6,991,888 B2 | 1/2006 | Padmanaban et al. |
| 9,063,414 B2 | 6/2015 | Ichikawa et al. |
| 9,372,402 B2 | 6/2016 | Freedman et al. |
| 9,389,506 B2 | 7/2016 | Chang et al. |
| 9,448,475 B2 | 9/2016 | Masuyama et al. |
| 10,040,812 B2 | 8/2018 | Matousek et al. |
| 11,829,069 B2 | 11/2023 | Kaitz et al. |
| 2018/0136558 A1 | 5/2018 | Hatakeyama |
| 2019/0155152 A1 | 5/2019 | Aqad et al. |
| 2019/0204743 A1 * | 7/2019 | Kaitz .................. G03F 7/2006 |
| 2020/0010594 A1 * | 1/2020 | Masuyama ............ C08F 220/38 |
| 2020/0231720 A1 * | 7/2020 | Masuyama ............ G03F 7/0045 |

FOREIGN PATENT DOCUMENTS

| JP | 4774996 | 9/2011 | |
| JP | 2014148494 | 8/2014 | |
| JP | 2020098332 A * | 6/2020 | ............ G03F 7/004 |
| KR | 20190082672 A | 7/2019 | |
| WO | WO2018/147094 * | 8/2018 | ............ G03F 7/038 |

OTHER PUBLICATIONS

English Translation of Japanese Patent Publication No. 2020098332-A (Year: 2020).*
Biafore et al. "Statistical simulation of resist at EUV and ArF" Advances in Resist Materials and Processing Technology XXVI, 7273: 727343, 11 pages (2009).
De Bisschop, P. "Stochastic effects in EUV lithography: random, local CD variability, and printing failures" J. Micro/Nanolith, 16(4): 041013, 18 pages (2017).
De Bisschop et al. "Stochastic effects in EUV Lithography" Proc. SPIE 10583, Extreme Ultraviolet (EUV) Lithography IX, 105831K, 18 pages (2018).
Closser et al. "The importance of inner-shell electronic structure for enhancing the EUV absorption of photoresist materials" J. Chem. Phys., 146(16): 164106, 14 pages (2017).
Georgiadou et al. "Effect of triphenylsulfonium triflate addition in wide band-gap polymer light-emitting diodes: improved charge injection, transport and electroplex-induced emission tuning" RSC Advances, 2: 11786-11792 (2012).
Grzeskowiak et al. "Polymer effects on PAG acid yiel in EUV resists" Proc. SPIE 10586, Advances in Patterning Materials and Processes XXXV, 105860D, 8 pages (2018).
Henke et al. "X-Ray X-Ray Interactions: Photoabsorption, Scattering, Transmission and Reflection E=50-30,000 eV, Z=1-92" Atomic Data and Nuclear Data Tables, 54: 181-342 (1993).
Higgins et al. "Resolution, Line-Edge Roughness, Sensitivity Tradeoff, and Quantum Yield of High Photo Acid Generator Resists for Extreme Ultraviolet Lithography" Japanese Journal of Applied Physics, 50(3R): 036504, 9 pages (2011).

(Continued)

Primary Examiner — Daborah Chacko-Davis
(74) Attorney, Agent, or Firm — Myers Bigel, P.A.

(57) ABSTRACT

Disclosed are resist compositions and semiconductor device fabrication methods wing the same. The resist composition comprises a hypervalent iodine compound of Chemical Formula 1 below. Wherein $R_1$ to $R_7$ are as defined herein.

[Chemical Formula 1]

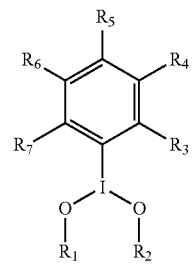

22 Claims, 4 Drawing Sheets

(56) References Cited

OTHER PUBLICATIONS

Kostko et al. "Fundamental understanding of chemical processes in extreme ultraviolet resist materials" J. Chem Phy., 149(15): 154305, 10 pages (2018).

Kozawa et a. "Radiation Chemistry in Chemically Amplified Resists" Japanese Journal of Applied Physics, 49(3R): 030001, 20 pages (2010).

Narasimhan et al. "Mechanisms of EUV Exposure: Electrons and Holes" Proc. of SPIE vol. 10143, 101430W, 10 pages (2017).

Fujii et al. "Patterning performance of chemically amplified resist in EUV lithography" Extreme Ultraviolet (EUV) Lithography VII, Proc. Of SPIE vol. 9776, 97760Y, 7 pages (2016).

* cited by examiner

RESIST COMPOSITIONS AND SEMICONDUCTOR FABRICATION METHODS USING THE SAME

CROSS-REFERENCE TO RELATED APPLICATION

This U.S. nonprovisional application claims priority under 35 U.S.C § 119 to Korean Patent Application No. 10-2019-0168997 filed on Dec. 17, 2019 in the Korean Intellectual Property Office, the disclosure of which is hereby incorporated by reference in its entirety.

BACKGROUND

The present inventive concepts relate to a resist composition and a pattern formation method using the same, and more particularly, to an extreme ultraviolet photoresist composition and a pattern formation method using the same.

Semiconductor devices have been highly integrated for high performance and low manufacture costs. An increase in integration of semiconductor devices may be achieved by precise patterning layers during fabricating semiconductor devices. Exposure and development processes using photoresist layers may be performed to pattern layers.

SUMMARY

Some example embodiments of the present inventive concepts provide a semiconductor device fabrication method with increased precision for a patterning process.

Some example embodiments of the present inventive concepts provide a pattern formation method in which a fine pitch pattern is formed with high accuracy.

According to some example embodiments of the present inventive concepts, a resist composition may include a hypervalent iodine compound of Chemical Formula 1 below.

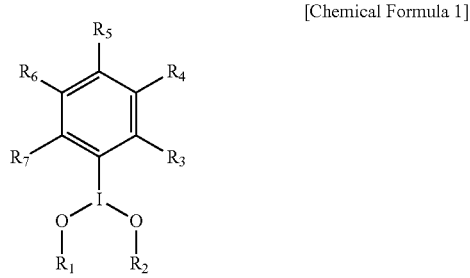

[Chemical Formula 1]

In Chemical Formula 1, $R_1$ may be hydrogen, $R_8CO_2^-$, or $R_9SO_2^-$. $R_2$ may be $R_{10}CO_2^-$ or $R_{11}SO_2^-$. $R_3$, $R_4$, $R_5$, $R_6$, and $R_7$ may each independently be a hydrogen, a halogen, a halogen-substituted C1 or C2 alkyl group, or a halogen-substituted C6 to C20 aryl group. $R_8$, $R_9$, $R_{10}$, and $R_{11}$ may each independently be a substituted or unsubstituted C1 or C2 alkyl group or a substituted or unsubstituted C6 to C20 aryl group.

According to some example embodiments of the present inventive concepts, a semiconductor device fabrication method may include: coating on a substrate a composition to form a resist layer; and patterning the resist layer.

The composition may include a hypervalent iodine compound of Chemical Formula 1 below.

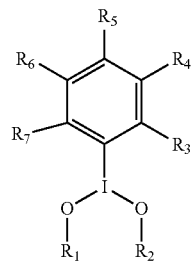

[Chemical Formula 1]

In Formula 1, $R_1$ may be a hydrogen, $R_8CO_2^-$, or $R_9SO_2^-$. $R_2$ may be $R_{10}CO_2^-$ or $R_{11}SO_2^-$. $R_3$, $R_4$, $R_5$, $R_6$, and $R_7$ may each be hydrogen. $R_8$ and $R_9$ may each be independently a halogen-substituted or halogen-unsubstituted C1 or C2 alkyl group or a halogen-substituted or halogen-unsubstituted C6 to C20 aryl group. $R_{10}$ may be an unsubstituted C1 or C2 alkyl group or an unsubstituted C6 to C20 aryl group. $R_{11}$ may be a halogen-substituted or halogen-unsubstituted C1 or C2 alkyl group or a halogen-substituted or halogen-unsubstituted C6 to C20 aryl group.

DETAILED DESCRIPTION

Figure 1:
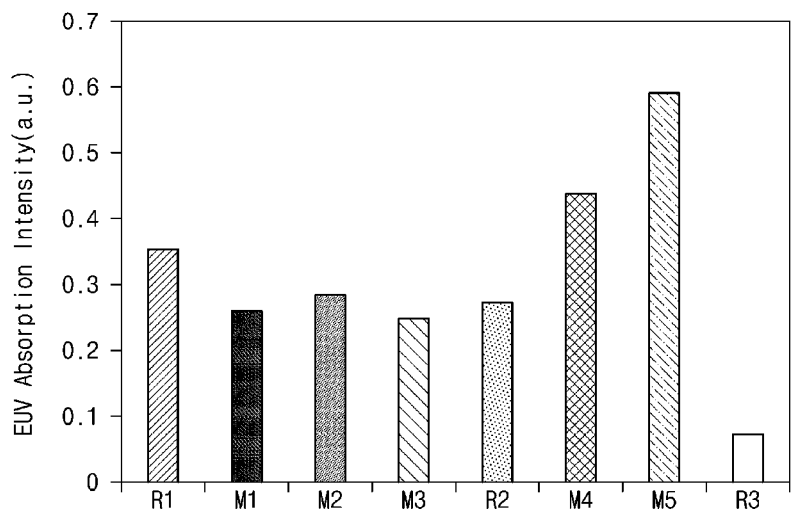
FIG. 1 illustrates a graph showing EUV absorption intensity of compounds of Chemical Formulae M1 to M5 and Comparative Examples.

In this description, the language "unsubstituted or substituted" may mean "unsubstituted or substituted with at least one substituent selected from deuterium atoms, halogen atoms, hydroxyl group, alkoxy group, ether group, halogenated alkyl group, halogenated alkoxy group, halogenated ether group, alkyl group, alkenyl group, aryl group, cyclic hydrocarbon group, and heterocyclic group. In addition, each substituent mentioned above may be substituted or unsubstituted. For example, a halogenated alkyl group may be referred to as an alkyl group.

In this description, a halogen element may be fluorine, chlorine, iodine, or bromine.

In this description, an alkyl group may be a straight, branched, or cyclic alkyl group. The number of carbon atoms in an alkyl group may be 1 or 2 (also referred to herein as a C1 or C2 alkyl group), but the present inventive concepts are not limited thereto. Examples of an alkyl group may be a methyl group and an ethyl group, but the present inventive concepts are not limited thereto.

In this description, an aryl group may include a substituted or unsubstituted aryl group. The number of carbon atoms in an aryl group may be 6 to 20 (also referred to herein as a C6 to C20 aryl group).

Unless defined otherwise in this description, when no chemical bond is drawn at a position in chemical formulae, a hydrogen atom may be bonded to the position to which the chemical bond is supposed to be given.

In this description, like reference numerals may indicate like components.

The following will now describe a composition, a pattern formation method using the composition, and a semiconductor device fabrication method using the composition.

According to the present inventive concepts, the composition may be a resist composition. The composition may be used to form patterns or to fabricate semiconductor devices. For example, the resist composition may be used in patterning processes for semiconductor device fabrication. The resist composition may be an extreme ultraviolet (EUV) resist composition or an electron-beam resist composition. The EUV may refer to an ultraviolet ray whose wavelength falls within a range of about 10 nm to about 124 nm, more narrowly of about 13.0 nm to about 13.9 nm, much more narrowly of about 13.4 nm to about 13.6 nm. The EUV may refer to light whose energy ranges from about 6.21 eV to about 124 eV, more narrowly about 90 eV to about 95 eV. The resist composition according to some embodiments may be a chemical amplified resist (CAR) type composition.

In some embodiments, the resist composition may include a polymer and a hypervalent iodine compound. The resist composition may further include a quencher. The hypervalent iodine compound may be a compound of Chemical Formula 1 below.

[Chemical Formula 1]

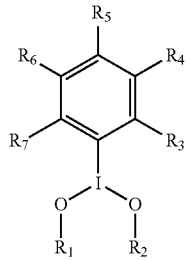

In Chemical Formula 1, $R_1$ may be hydrogen, $R_8CO_2^-$, or $R_9SO_2^-$; $R_2$ may be $R_{10}CO_2^-$ or $R_{11}SO_2^-$; $R_3$, $R_4$, $R_5$, $R_6$, and $R_7$ may each independently be a hydrogen, a halogen, a halogen-substituted C1 or C2 alkyl group, or a halogen-substituted C6 to C20 aryl group; and $R_8$, $R_9$, $R_{10}$, and $R_{11}$ may each independently be a substituted or unsubstituted C1 or C2 alkyl group or a substituted or unsubstituted C6 to C20 aryl group.

In some embodiments, in $R_8$, $R_9$, $R_{10}$, and $R_{11}$ of Chemical Formula 1, the substituted alkyl group may include a halogen-substituted alkyl group, and the substituted aryl group may include a halogen-substituted aryl group.

In some embodiments, one or more of $R_1$ and $R_2$ may include no hydrogen. For example, in Chemical Formula 1, $R_1$ may include $R_8CO_2^-$ or $R_9SO_2^-$, or $R_2$ may include $R_{10}CO_2^-$ or $R_{11}SO_2^-$. $R_8$, $R_9$, $R_{10}$, and $R_{11}$ may be the same as those defined above.

In some embodiments, the polymer may be a photoresist material. For example, the polymer may include a compound of Chemical Formula 2A below, but the present inventive concepts are not limited thereto.

[Chemical Formula 2A]

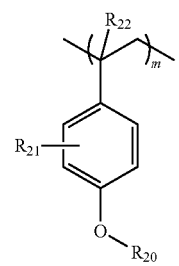

In Chemical Formula 2A, $R_{20}$, $R_{21}$, and $R_{22}$ may each independently be hydrogen or a substituted or unsubstituted C1 to C15 alkyl group, and m may be an integer between 10 and 1,000,000.

In some embodiments, the polymer may include a compound of Chemical Formula 2B below.

[Chemical Formula 2B]

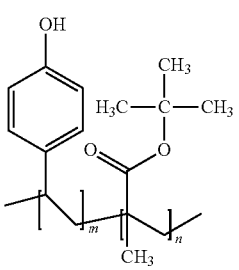

In Chemical Formula 2B, m may be an integer between 10 and 1,000, and n may be an integer of from 10 to 1,000.

In some embodiments, the resist composition may further include a photo-acid generator. The photo-acid generator may generate hydrogen ions in a subsequent exposure process. For example, the photo-acid generator may include one or more of a compound of Chemical Formula 3A below and a compound of Chemical Formula 3B below. The material represented by Chemical Formula 3A may be referred to as diphenyliodonium triflate (DPT-Tf), and the material represented by Chemical Formula 3B may be referred to as triphenylsulfonium triflate (TPS-Tf).

[Chemical Formula 3A]

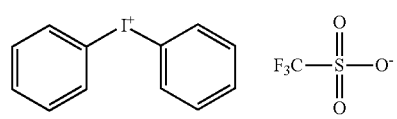

[Chemical Formula 3B]

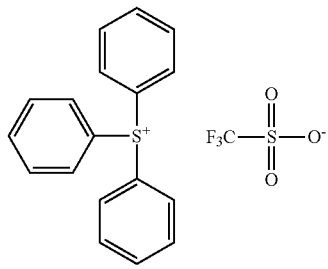

When the hypervalent iodine compound serves as an additive, the resist composition may further include the photo-acid generator. When the hypervalent iodine compound serves as a photo-acid generator, the resist composition may include no additional photo-acid generator. In some embodiments, even though the hypervalent iodine compound serves as a photo-acid generator, the resist composition may further include the compound of Chemical Formula 3A and/or the compound of Chemical Formula 3B.

The quencher may be, for example, a photo-decomposable quencher (PDQ). The quencher may include a base material. For example, the quencher may include an amine, for example, a tertiary amine. The tertiary amine may include 10 to 100 carbon atoms, but the present inventive concepts are not limited thereto. The quencher may include, for example, one or more of a compound of Chemical Formula 4A below and a compound of Chemical Formula 4B below. The compound of Chemical Formula 4A may be tri (n-octyl) amine. The compound of Chemical Formula 4B may be 1,8-diazabicyclo[5.4.0]undec-7-ene (DBU).

[Chemical Formula 4A]

CH₃(CH₂)₆CH₂—N(CH₂(CH₂)₆CH₃)—CH₂(CH₂)₆CH₃

[Chemical Formula 4B]

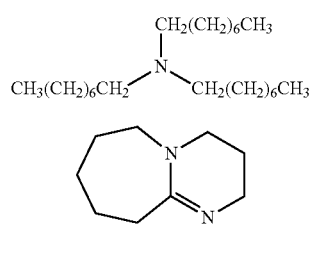

The following will describe in detail the hypervalent iodine compound according to some example embodiments.

In some embodiments, in Chemical Formula 1, $R_1$ may be hydrogen, $R_8CO_2^-$ or $R_9SO_2^-$, $R_2$ may be $R_{10}CO_2^-$ or $R_{11}SO_2^-$, $R_3$, $R_4$, $R_5$, $R_6$, and $R_7$ may each independently be hydrogen, $R_8$ and $R_9$ may each independently be a halogen-substituted or halogen-unsubstituted C1 or C2 alkyl group or a halogen-substituted or halogen-unsubstituted C6 to C20 aryl group, $R_{10}$ may be an unsubstituted C1 or C2 alkyl group or an unsubstituted C6 to C20 aryl group, and $R_{11}$ may be a halogen-substituted or halogen-unsubstituted C1 or C2 alkyl group or a halogen-substituted or halogen-unsubstituted C6 to C20 aryl group.

In some embodiments, the hypervalent iodine compound of Chemical Formula 1 may serve as an additive. When the hypervalent iodine compound serves as an additive, the hypervalent iodine compound may have a high LUMO (lowest unoccupied molecular orbital) energy level. During an exposure process performed on a resist layer, the polymer may absorb light to emit secondary electrons. The light may be an extreme ultraviolet ray. One or more of the secondary electrons may be transferred and trapped by the photo-acid generator. The photo-acid generator may decompose the transferred secondary electrons and may generate hydrogen ions (H⁺). Under the presence of the secondary electron and the photo-acid generator, the hypervalent iodine compound may act as an acid to accelerate the generation of hydrogen ions. An exposure process of a resist layer may mainly depend on transfer efficiency of the secondary electron. For example, an increase in the transfer efficiency of the secondary electron may improve patterning precision and accuracy. In some embodiments, the hypervalent iodine compound may cause an enhancement in transfer efficiency of the secondary electron.

In performing an exposure process on a resist layer, an increase in generation of the secondary electron may improve efficiency and accuracy of the exposure process. Because the hypervalent iodine compound has high light absorption, the hypervalent iodine compound may absorb light to increase generation of the secondary electron.

For example, the compound of Chemical Formula 1 may be one of compounds of Chemical Formulae M1, M2, and M3 below.

[Chemical Formula M1]

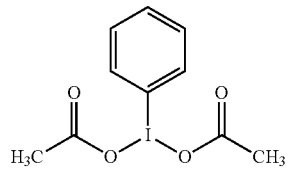

[Chemical Formula M2]

[Chemical Formula M3]

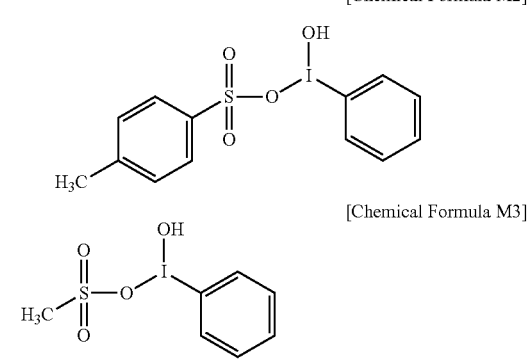

Each of the hypervalent iodine compounds of Chemical Formulae M1, M2, and M3 may serve as an additive.

Table 1 lists LUMO energy levels of the compound of Chemical Formula M1, the compound of Chemical Formula M2, the compound of Chemical Formula M3, and the photo-acid generator.

TABLE 1

| | Compound | LUMO energy level (eV) |
|---|---|---|
| Embodiment | Chemical Formula M1 | −1.03 |
| | Chemical Formula M2 | −0.89 |
| | Chemical Formula M3 | −0.89 |
| Photo-acid generator | diphenyliodonium triflate (DPT-Tf) | −1.31 |
| | triphenylsulfonium triflate (TPS-Tf) | −1.13 |

Referring to Table 1, the hypervalent iodine compound may have a high LUMO energy level. Each of the compounds of Chemical Formulae M1, M2, and M3 may have an LUMO energy level higher than that of the photo-acid generator. For example, the hypervalent iodine compound may have the LUMO energy level higher than that of diphenyliodonium triflate and that of triphenylsulfonium triflate. The LUMO energy level of the hypervalent iodine compound may be equal to or greater than about −1.12 eV. Therefore, the hypervalent iodine compound may accelerate transfer of the secondary electron toward the photo-acid generator. When the hypervalent iodine compound has a LUMO energy level (e.g., less than about −1.12 eV) lower than that of the photo-acid generator, the hypervalent iodine compound may not assist the transfer of the secondary electron.

The hypervalent iodine compound may have electron-trap decomposition properties, and thus may be decomposed to generate hydrogen ions under secondary-electron trap condition. However, the hypervalent iodine compound may have stability against heat and chemicals in performing an exposure process on a resist layer.

In some embodiments, the hypervalent iodine compound may have a conjugation structure. Therefore, the hypervalent iodine compound may have excellent interaction with one or more of the polymer and the photo-acid generator.

Table 2 shows binding energies between the hypervalent iodine compound and the photo-acid generator. The binding energy may be intermolecular interaction energy between the hypervalent iodine compound and the photo-acid generator. The binding energy may not be covalent bond energy.

TABLE 2

| | Binding Energy (Kcal/mol) |
|---|---|
| Chemical Formula M1 and diphenyliodonium triflate | 15.4 |
| Chemical Formula M1 and triphenylsulfonium triflate | 16.9 |
| Chemical Formula M3 and diphenyliodonium triflate | 17.5 |
| Chemical Formula M3 and triphenylsulfonium triflate | 18.7 |

Referring to Table 2, it may be ascertained that a relatively large binding energy is provided between diphenyliodonium triflate and the compound of Chemical Formula M1, between triphenylsulfonium triflate and the compound of Chemical Formula M1, between diphenyliodonium triflate and the compound of Chemical Formula M3, and between triphenylsulfonium triflate and the compound of Chemical Formula M3. In some embodiments, the binding energy between the hypervalent iodine compound and the photo-acid generator may be equal to or greater than about 15.4 Kcal/mol. When the binding energy between the hypervalent iodine compound and the photo-acid generator satisfies the condition above, the hypervalent iodine compound may have excellent interaction with the photo-acid generator, and the secondary electron may be effectively transferred through the hypervalent iodine compound toward the photo-acid generator. When the binding energy satisfies the condition above, although the resist composition includes the hypervalent iodine compound and the photo-acid generator, no phase separation may occur between the hypervalent iodine compound and iodine.

The following will discuss various hypervalent iodine compounds according to some example embodiments.

In some embodiments, in Chemical Formula 1, $R_1$ may be $R_8CO_2$— or $R_9SO_2$—, $R_2$ may be $R_{10}CO_2^-$ or $R_{11}SO_2^-$, $R_3$, $R_4$, $R_5$, $R_6$, and $R_7$ may each independently be hydrogen, halogen, a halogen-substituted C1 or C2 alkyl group, or a halogen-substituted C6 to C20 aryl group, and $R_8$, $R_9$, $R_{10}$, and $R_{11}$ may each independently be a halogen-substituted or unsubstituted C1 or C2 alkyl group or a halogen-substituted or unsubstituted C6 to C20 aryl group.

In this case, the hypervalent iodine compound of Chemical Formula 1 may serve as a photo-acid generator, and thus may generate hydrogen ions in performing an exposure process on a resist layer. For example, a hypervalent iodine compound of Chemical Formula M4 below and a hypervalent iodine compound of Chemical Formula M5 below may each serve as a photo-acid generator.

In some embodiments, the hypervalent iodine compound may have a low LUMO energy level. For example, the compound of Chemical Formula 1 may have the LUMO energy level lower than that of diphenyliodonium triflate and that of triphenylsulfonium triflate. The hypervalent iodine compound may have dissociation energy properties. Therefore, in performing an exposure process on a resist layer, the hypervalent iodine compound may be decomposed by the secondary electron, thereby generating hydrogen ions.

For example, the compound represented by Chemical Formula 1 may include a compound of Chemical Formula M4 or Chemical Formula M5.

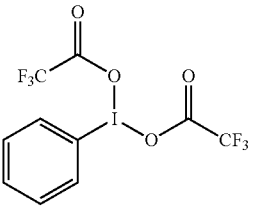

[Chemical Formula M4]

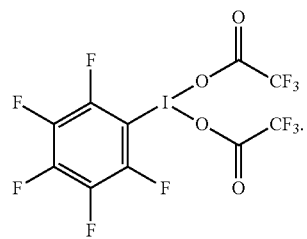

[Chemical Formula M5]

The hypervalent iodine compound of Chemical Formula M4 and the hypervalent iodine compound of Chemical Formula M5 may each serve as a photo-acid generator.

Table 3 lists LUMO energy levels of the compound of Chemical Formula M4, of the compound of Chemical Formula M5, and of the photo-acid generator.

TABLE 3

| | Compound | LUMO energy level (eV) |
|---|---|---|
| Embodiment | Chemical Formula M4 | −1.73 |
| | Chemical Formula M5 | −2.18 |
| Comparative | diphenyliodonium triflate (DPT-Tf) | −1.31 |
| | triphenylsulfonium triflate (TPS-Tf) | −1.13 |

Referring to Table 3, the hypervalent iodine compound according to some example embodiments may have an LUMO energy level lower than that of diphenyliodonium triflate and that of triphenylsulfonium triflate. For example, the compound of Chemical Formula M4 and the compound of Chemical Formula M5 may each have the LUMO energy level equal to or less than about −1.14 eV. Therefore, in comparison with diphenyliodonium triflate and triphenylsulfonium triflate, the hypervalent iodine compound may readily receive the secondary electron. When the hypervalent iodine compound has a LUMO energy level (e.g., greater than about −1.14 eV) higher than that of the photoacid generator, the hypervalent iodine compound may not act as a photo-acid generator.

The following will describe detailed properties of the hypervalent iodine compound according to some example embodiments. The below-described properties of the hypervalent iodine compound may be applicable when the hypervalent iodine compound serves as an additive in a composition and when the hypervalent iodine compound serves as a photo-acid generator. For example, unless otherwise stated, the below-described properties of the hypervalent iodine compound may indicate properties of each of the compounds of Chemical Formulae M1 to M5.

(1) EUV Absorption

In performing an exposure process on a resist layer, an increase in generation of the secondary electron may improve efficiency and accuracy of the exposure process. In some embodiments, the hypervalent iodine compound may have improved EUV absorption properties. The EUV absorption properties may be evaluated with EUV absorption coefficient.

FIG. 1 illustrates a graph showing EUV absorption intensity of compounds of Chemical Formulae M1 to M5 and Comparative Examples. In FIG. 1, the symbols M1, M2, M3, M4, and M5 refer to the compounds of Chemical Formulae M1, M2, M3, M4, and M5, respectively, and Comparative Examples may include diphenyliodonium triflate represented as R1, triphenylsulfonium triflate represented as R2, and phenol represented as R3.

Referring to FIG. 1, the compounds M1 to M5 of Chemical Formulae M1 to M5 may have their EUV absorption intensity greater than that of R3 (i.e., phenol). The compounds M4 and M5 of Chemical Formulae M4 and M5 may have their EUV absorption intensity greater than that of R1 (i.e., diphenyliodonium triflate) and that of R2 (i.e., triphenylsulfonium triflate). Because the compounds M4 and M5 of Chemical Formulae M4 and M5 have their high EUV absorption intensity, the resist composition may excellently absorb light in an EUV wavelength range during an exposure process.

(2) Stability

[Stability in Chemical Environment]

In some embodiments, the hypervalent iodine compound may be stable in the chemical environment. The phrase "is stable in the chemical environment" may mean that there is no or extremely low reactivity with respect to the atmosphere, a dimethyl sulfoxide (DMSO) solution, an amine-containing material such as a trimethyl amine solution, and a cresol solution. In this description, the language "atmosphere" may be defined to include about 80% nitrogen ($N_2$) and about 20% oxygen ($O_2$). The reactivity may be evaluated with dissociation energy. A dissociation reaction may cause the hypervalent iodine compound to produce cations and anions. The dissociation reaction of the hypervalent iodine compound may be shown as Equation 1 below. For example, dissociation reaction energy may be defined as the dissociation energy.

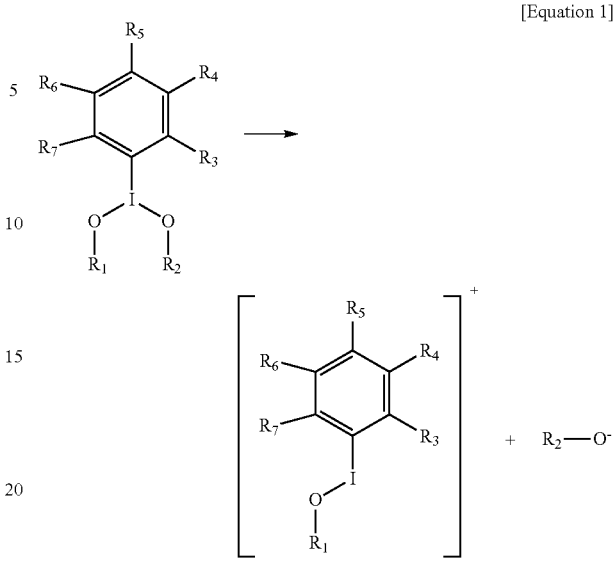

[Equation 1]

In Equation 1, $R_1$ to $R_7$ may be the same as those defined herein in Chemical Formula 1.

For example, the dissociation reaction of the compound of Chemical Formula M2 may be shown as Equation 1A below.

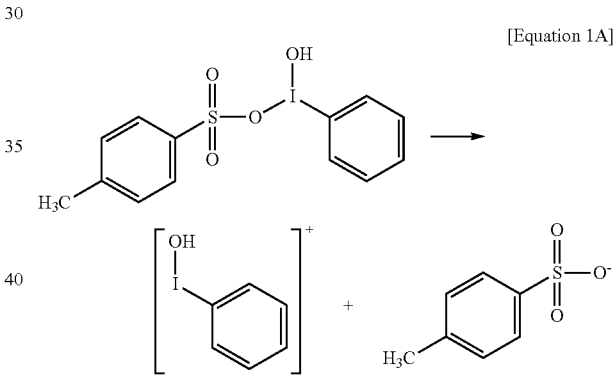

[Equation 1A]

Figure 2:
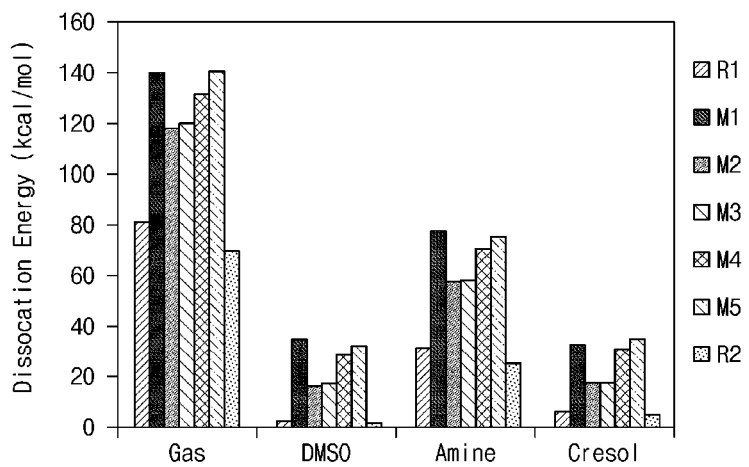
FIG. 2 illustrates a graph showing dissociation energy of compounds of Chemical Formulae M1 to M5 and Comparative Examples.

FIG. 2 illustrates a graph showing dissociation energies of compounds of Chemical Formulae M1 to M5 and Comparative Examples. In FIG. 2, the symbols M1, M2, M3, M4, and M5 may refer to the compounds of Chemical Formulae M1, M2, M3, M4, and M5, respectively, and Comparative Examples may include diphenyliodonium triflate represented as R1 and triphenylsulfonium triflate represented as R2. The dissociation energy may be a result obtained by subtracting energy of a starting material from a sum of energies of the produced cations and anions.

Referring to FIG. 2, the compounds M1 to M5 of Chemical Formulae M1 to M5 may have their dissociation energy greater than that of R1 (i.e., diphenyliodonium triflate) and that of R2 (i.e., triphenylsulfonium triflate). This property that the compounds M1 to M5 of Chemical Formulae M1 to M5 have their large dissociation energy may be found in the atmosphere, a dimethyl sulfoxide (DMSO) solution, an amine-containing material such as a trimethyl amine solution, and a cresol solution. Each of the compounds M1 to M5 of Chemical Formulae M1 to M5 may be dissociated to produce cations and anions. Because the cations and anions are relatively stable, the compounds M1 to M5 of Chemical Formulae M1 to M5 may have their relatively large dissociation energy. It may be ascertained that the compounds M1 to M5 of Chemical Formulae M1 to M5 may have their superior stability in various chemical environments.

[Thermal Stability]

The hypervalent iodine compound may be thermally stable.

Table 4 lists melting points of the compounds of Chemical Formulae M1 to M5.

TABLE 4

| | Compound | Melting Point (° C.) |
|---|---|---|
| Embodiment | Chemical Formula M1 | 163-165 |
| | Chemical Formula M2 | 131-137 |
| | Chemical Formula M3 | 120-124 |
| | Chemical Formula M4 | 121-125 |
| | Chemical Formula M5 | 117-119 |

Referring to Table 4, the hypervalent iodine compound may have a relatively high melting point. The hypervalent iodine compound may have a solid or crystalline state at room temperature (e.g., about 25° C.). The hypervalent iodine compound may have a melting point of, for example, greater than about 100° C. Therefore, the hypervalent iodine compound may be thermally stable.

(3) Generation of Acid (H$^+$) Under Secondary-Electron Trap Condition

In some embodiments, the hypervalent iodine compound may react with the polymer or the photo-acid generator under secondary-electron trap condition, thereby producing hydrogen ions. The hypervalent iodine compound may serve to produce acid.

For example, a reaction for the hydrogen ion generation from the hypervalent iodine compound may be shown in Equation 2 below.

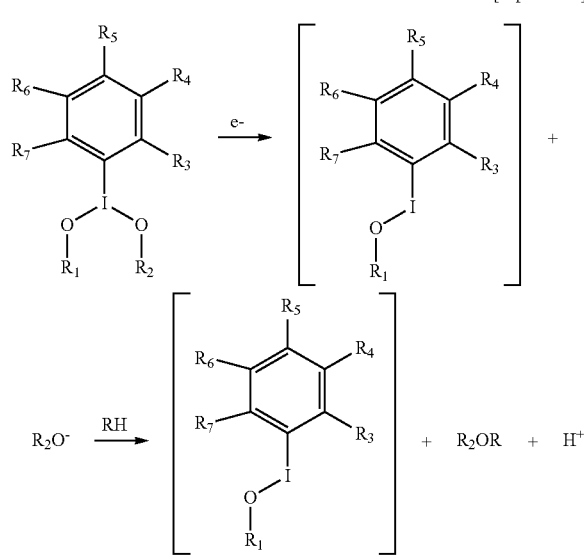

[Equation 2]

In Equation 2, $R_1$ to $R_7$ may be the same as those defined herein in Chemical Formula 1, e$^-$ may be the secondary electron, RH may be one of the polymer of Chemical Formula 2A, the polymer of Chemical Formula 2B, diphenyliodonium triflate, and triphenylsulfonium triflate.

For example, a reaction for the hydrogen ion generation from the compound of Chemical Formula M2 may be shown as Equation 2A below.

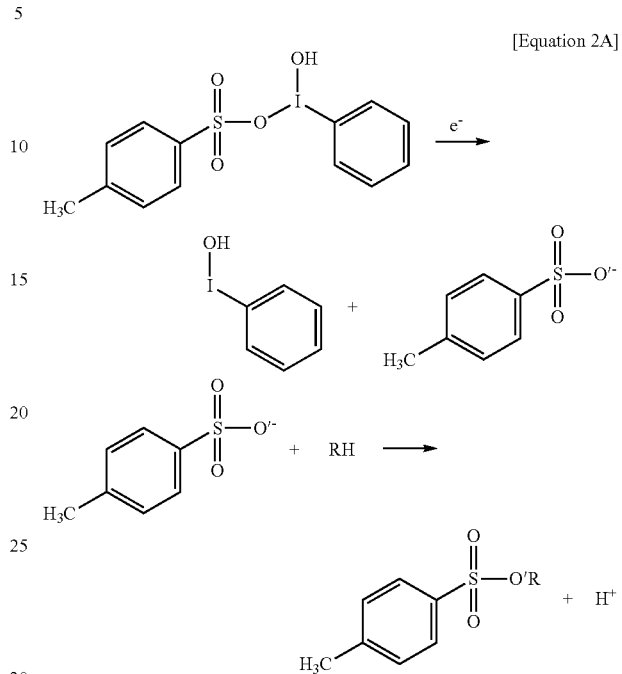

[Equation 2A]

In Equation 2A, e$^-$ may be the secondary electron, and RH may be one of the polymer of Chemical Formula 2A, the polymer of Chemical Formula 2B, diphenyliodonium triflate, and triphenylsulfonium triflate.

Figure 3:
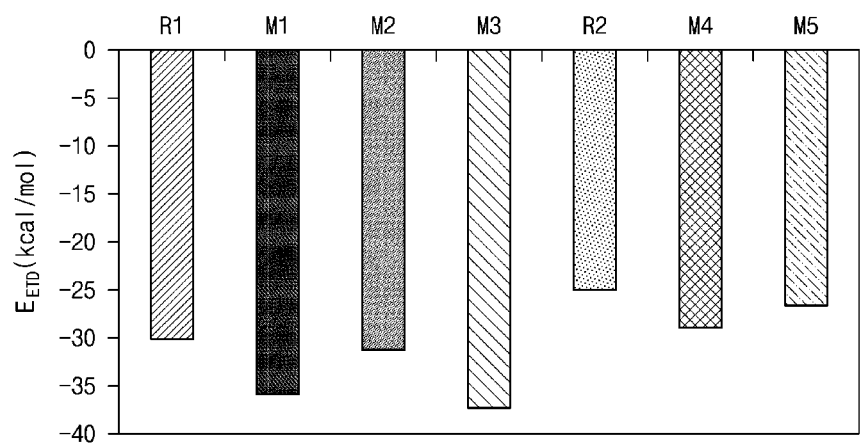
FIG. 3 illustrates a graph showing electron-trap decomposition energy of compounds of Chemical Formulae M1 to M5 and Comparative Examples.

FIG. 3 illustrates a graph showing electron-trap decomposition energy $E_{ETD}$ of compounds of Chemical Formulae M1 to M5 and Comparative Examples. In FIG. 3, the symbols M1, M2, M3, M4, and M5 may refer to the compounds of Chemical Formulae M1, M2, M3, M4, and M5, respectively, and Comparative Examples may include R1 (i.e., diphenyliodonium triflate) and R2 (i.e., triphenylsulfonium triflate). The electron-trap decomposition energy may be a result obtained by subtracting energy of a target material at its excited state from a total sum of energies of materials produced after decomposition.

Referring to FIG. 3, the more negative value of the electron-trap decomposition energy, the larger decomposition rate of the target material under secondary-electron trap condition. The compounds M1 to M5 of Chemical Formulae M1 to M5 may have their electron-trap decomposition energy of about −25 Kcal/mol or less. The compounds M1 to M5 of Chemical Formulae M1 to M5 may have their hydrogen-trap decomposition energy whose negative value is less than that of hydrogen-trap energy. The compounds M1 to M5 of Chemical Formulae M1 to M5 may have their electron-trap decomposition energy whose negative value is less than that of electron-trap decomposition energy of R1 (i.e., diphenyliodonium triflate).

In some embodiments, an increase in transfer efficiency of the secondary electron may improve patterning precision and accuracy. Under secondary-electron trap condition, the compounds M1 to M5 of Chemical Formulae M1 to M5 may be promptly decomposed due to their reaction with the secondary electron, thereby producing hydrogen ions. Because the compounds M1 to M5 of Chemical Formulae M1 to M5 promptly react with the secondary electron, the secondary electron may increase in transfer efficiency.

The following will describe a pattern formation method and a semiconductor device fabrication method that use a resist compound according to some embodiments of the present inventive concepts.

Figure 4:
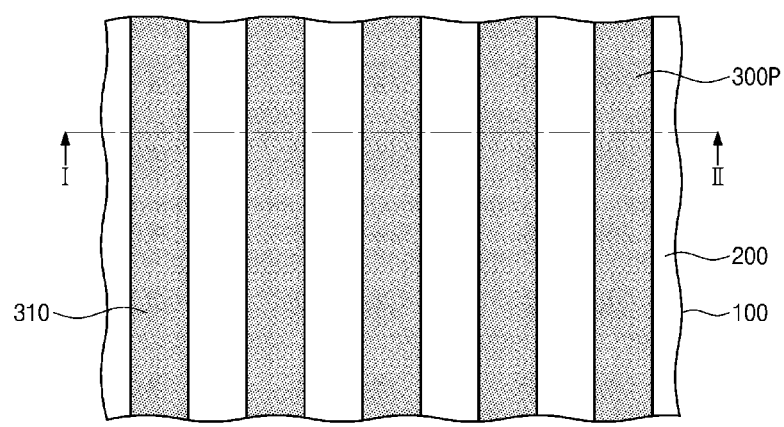
FIG. 4 illustrates a plan view showing a resist pattern according to some example embodiments of the present inventive concepts.

FIG. 4 illustrates a plan view showing a resist pattern according to some example embodiments of the present inventive concepts. FIGS. 5 to 8 illustrate cross-sectional views taken along line I-II of FIG. 4, showing a semiconductor device fabrication method according to some example embodiments of the present inventive concepts.

Figure 5:
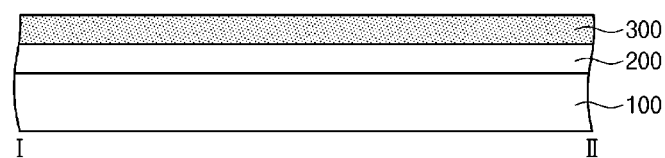
FIGS. 5 to 8 illustrate cross-sectional views showing a semiconductor device fabrication method according to some example embodiments of the present inventive concepts.

Referring to FIG. 5, a substrate 100 may be prepared. A lower layer 200 and a resist layer 300 may be sequentially formed on the substrate 100. The lower layer 200 may be an etching target. The lower layer 200 may include a semiconductor material, a conductive material, a dielectric material, or any combination thereof. In addition, the lower layer 200 may be formed of a single layer or a plurality of stacked layers. Although not shown, one or more layers may further be provided between the substrate 100 and the lower layer 200.

A resist composition (or a resist compound) according to some example embodiments may be coated on the lower layer 200, thereby forming the resist layer 300. In some embodiments, a spin coating process may be performed to coat the resist composition. An annealing process may be further performed on the coated resist compound. The annealing process may correspond to a baking process of the resist layer 300.

Figure 6:
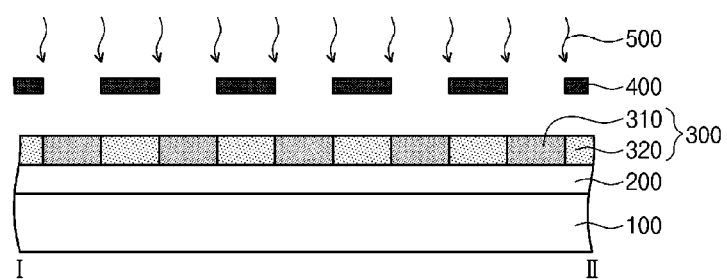

Referring to FIG. 6, the resist layer 300 may be exposed to light 500. The light 500 may be an electron beam or an extreme ultraviolet ray. Before the light 500 is irradiated, a photomask 400 may be disposed on the resist layer 300. The resist layer 300 may have a first portion 310 exposed by the photomask 400, and the light 500 may be irradiated on the first portion 310 of the resist layer 300.

When the resist layer 300 is exposed to the light 500, as discussed above, a polymer may absorb the light 500 to emit secondary electrons. An efficiency increase in generation and transfer of the secondary electron may result in a precise formation of the first portion 310 and an increase in efficiency of the exposure process. In some embodiments, a hypervalent iodine compound may include an iodine atom and may exhibit high extreme ultraviolet (EUV) adsorption. The secondary electrons may be transferred and trapped by a photo-acid generator. The photo-acid generator may decompose the transferred second electrons and may generate hydrogen ions ($H^+$). Under the presence of the secondary electron, the hypervalent iodine compound may react with the secondary electron, thereby generating the hydrogen ion. The hypervalent iodine compound may enhance transfer efficiency of the secondary electron. Because the resist composition includes the hypervalent iodine compound, the first portion 310 of the resist layer 300 may be promptly formed and may have a fine width.

A second portion 320 of the resist layer 300 may not be exposed to the light 500. The resist compound contained in the second portion 320 of the resist layer 300 may have an unchanged chemical structure. Therefore, after the irradiation of the light 500, the first portion 310 of the resist layer 300 may have a chemical structure different from that of the second portion 320. Thereafter, the photomask 400 may be removed.

Figure 7:
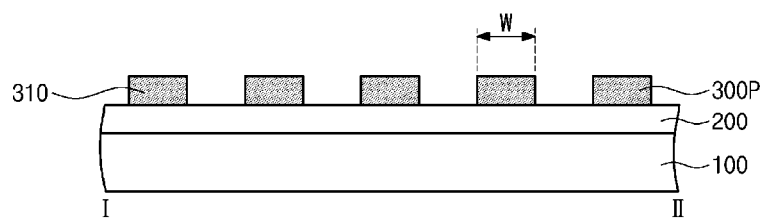

Referring to FIGS. 4 and 7, a developer may remove the second portion 320 of the resist layer 300, thereby forming a resist pattern 300P. The resist pattern 300P may be formed by a patterning process that includes exposure and development processes. The resist pattern 300P may correspond to the first portion 310 of the resist layer 300. The resist pattern 300P may be formed to have a fine width W and pitch.

The resist pattern 300P may have a linear shape when viewed in plan as shown in FIG. 4. For example, the resist pattern 300P may include extensions elongated in one direction. In some embodiments, the resist pattern 300P may have various shapes such as a zigzag shape, a honeycomb shape, or a circular shape, when viewed in plan. The resist pattern 300P may expose the lower layer 200.

Figure 8:
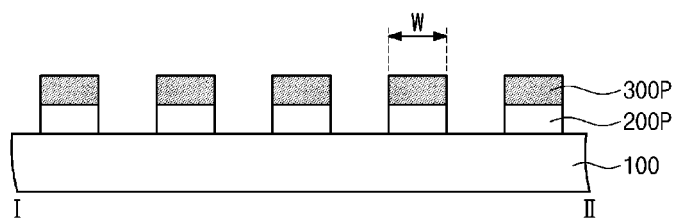

Referring to FIGS. 4 and 8, the lower layer 200 exposed by the resist pattern 300P may be removed to form a lower pattern 200P. An etching process may be performed to remove portions of the lower layer 200. The lower layer 200 may have an etch selectivity with respect to the resist pattern 300P. The lower pattern 200P may expose the substrate 100. In some embodiments, the lower pattern 200P may expose a layer interposed between the substrate 100 and the lower pattern 200P. Afterwards, the resist pattern 300P may be removed. Accordingly, the formation of a pattern may be completed. The pattern may indicate the lower pattern 200P. The lower pattern 200P may have a width that corresponds to the width W of the resist pattern 300P. Because the resist pattern 300P has the small width W, the lower pattern 200P may be formed to have a small width. The processes mentioned above may complete the patterning of the lower layer 200 and the formation of the lower pattern 200P.

In some embodiments, the lower pattern 200P may be a component of a semiconductor device. For example, the lower pattern 200P may be a semiconductor pattern, a conductive pattern, or a dielectric pattern of the semiconductor device.

Figure 9:
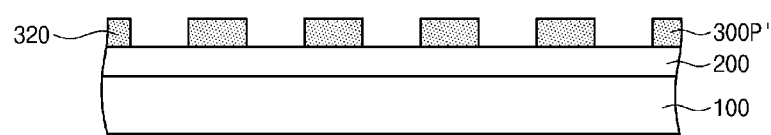
FIGS. 9 and 10 illustrate cross-sectional views showing a semiconductor device fabrication method according to some example embodiments of the present inventive concepts.
Figure 10:
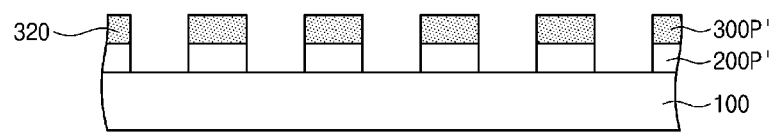

FIGS. 9 and 10 illustrate cross-sectional views showing a semiconductor device fabrication method according to some example embodiments of the present inventive concepts.

Referring again to FIG. 5, a resist layer 300 and a lower layer 200 may be formed on a substrate 100. The substrate 100, the lower layer 200, and the resist layer 300 may be substantially the same as those discussed above with reference to FIG. 5.

Referring again to FIG. 6, the resist layer 300 may be irradiated with light 500 on a first portion 310 thereof. After the irradiation of the light 500, a material of the first portion 310 may have a different chemical structure from that of a material of a second portion 320 of the resist layer 300.

Referring to FIG. 9, a developer may remove the first portion 310 of the resist layer 300, thereby forming a resist pattern 300P'. The developer may not remove the second portion 320 of the resist layer 300. The resist pattern 300P' may correspond to the second portion 320 of the resist layer 300.

Referring to FIG. 10, the lower layer 200 may be etched to form a lower pattern 200P'. The lower pattern 200P' may be formed on a position that corresponds to that of the second portion 320 of the resist pattern 300P'. The etching of the lower layer 200 may be substantially the same as that discussed above with reference to FIG. 8. Thereafter, the resist pattern 300P' may be removed.

In this description, A CAS Registry Number of the material represented by Chemical Formula M1 is 3240-34-4, a CAS Registry Number of the material represented by Chemical Formula M2 is 27126-76-7, and a CAS Registry Number of the material represented by Chemical Formula M3 is 105551-42-6. A CAS Registry Number of the material represented by Chemical Formula M4 is 2712-78-9, and a CAS Registry Number of the material represented by Chemical Formula M5 is 14353-88-9.

According to the present inventive concepts, a composition may include a hypervalent iodine compound. The composition may be used to form a resist pattern. The resist pattern may increase precision and/or accuracy. The resist pattern may also improve in formation efficiency.

The above-disclosed subject matter is to be considered illustrative, and not restrictive. Accordingly, the detailed description provided herein should not be construed as limited to embodiments set forth herein, and it is intended that the present inventive concepts cover the various combinations, the modifications and variations of example embodiments without departing from the scope of the present inventive concepts. The appended claims should be construed to include other embodiments.

What is claimed is:

1. An extreme ultraviolet (EUV) resist composition comprising a hypervalent iodine compound of Chemical Formula 1,

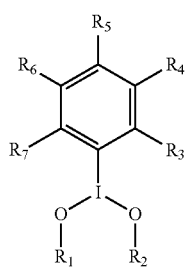

[Chemical Formula 1]

wherein:
R1 is hydrogen, R8CO—, or R9SO2-,
R2 is R10CO— or R11SO2-,
R3, R4, R5, R6, and R7 are each independently a hydrogen, a halogen, a halogen-substituted C1 or C2 alkyl group, or a halogen-substituted C6 to C20 aryl group, and
R8, R9, R10, and R11 are each independently a substituted or unsubstituted C1 or C2 alkyl group or a substituted or unsubstituted C6 to C20 aryl group
wherein the resist composition further comprises:
a quencher; and
a polymer comprising a compound of Chemical Formula 2A or 2B:

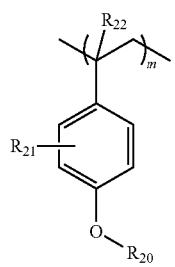

[Chemical Formula 2A]

wherein R20, R21, and R22 are each independently hydrogen or a substituted or unsubstituted C1 to C15 alkyl group, and m is an integer between 10 and 1,000,000, or

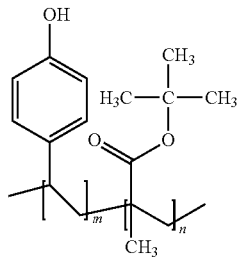

[Chemical Formula 2B]

wherein m is an integer between 10 and 1,000, and n is an integer between 10 to 1,000, wherein the resist composition forms a layer when exposed to EUV light at a wavelength of about 10 nm to about 124 nm.

2. The resist composition of claim 1, wherein one or both of $R_1$ and $R_2$ are devoid of hydrogen.

3. The resist composition of claim 1, wherein
R3, R4, R5, R6, and R7 are each hydrogen,
R8 and R9 are each independently a halogen-substituted or halogen-unsubstituted C1 or C2 alkyl group or a halogen-substituted or halogen-unsubstituted C6 to C20 aryl group,
R10 is an unsubstituted C1 or C2 alkyl group or an unsubstituted C6 to C20 aryl group, and
R11 is a halogen-substituted or halogen-unsubstituted C1 or C2 alkyl group or a halogen-substituted or halogen-unsubstituted C6 to C20 aryl group.

4. The resist composition of claim 3, wherein the hypervalent iodine compound includes a compound of Chemical Formula M2 or Chemical Formula M3,

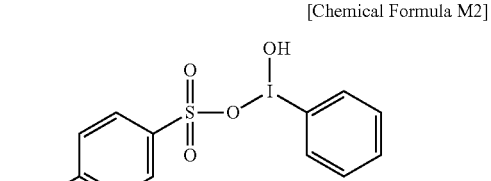

[Chemical Formula M2]

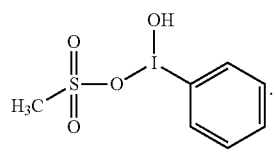

[Chemical Formula M3]

5. The resist composition of claim 3, further comprising a photo-acid generator,
wherein the compound of Chemical Formula 1 has a lowest unoccupied molecular orbital (LUMO) energy level that is greater than that of the photo-acid generator.

6. The resist composition of claim 5, wherein the compound of Chemical Formula 1 has the lowest unoccupied molecular orbital (LUMO) energy level that is equal to or greater than about −1.12 eV.

7. The resist composition of claim 1, wherein
R1 is R8CO— or R9SO2-, and
R8, R9, R10, and R11 are each independently a halogen-substituted or halogen-unsubstituted C1 and C2 alkyl group or a halogen-substituted or halogen-unsubstituted C6 to C20 aryl group.

8. The resist composition of claim 7, wherein the hypervalent iodine compound includes a compound of Chemical Formula M4,

[Chemical Formula M4]

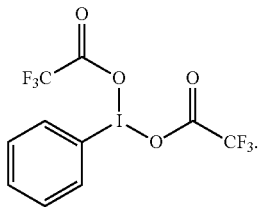

9. The resist composition of claim 7, wherein the hypervalent iodine compound includes a compound of Chemical Formula M5,

[Chemical Formula M5]

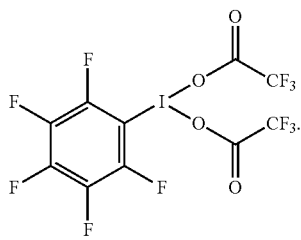

10. The resist composition of claim 7, wherein the compound of Chemical Formula 1 has a lowest unoccupied molecular orbital (LUMO) energy level that is less than that of diphenyliodonium triflate and that of triphenylsulfonium triflate.

11. The resist composition of claim 1, wherein the quencher includes a compound of Chemical Formula 4A or Chemical Formula 4B,

[Chemical Formula 4A]

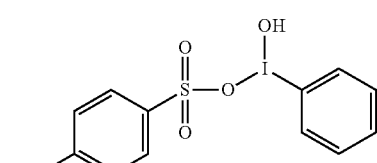

[Chemical Formula 4B]

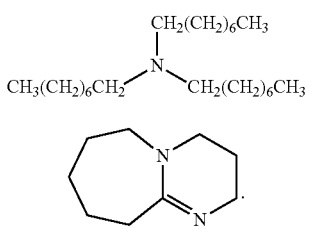

12. A semiconductor device fabrication method comprising:
  coating on a substrate a composition to form a resist layer; and
  patterning the resist layer,
  wherein the composition includes the resist composition of claim 1.

13. The method of claim 12, wherein patterning the resist layer includes:
  irradiating light on the resist layer; and
  using a developer to remove a portion of the resist layer,
  wherein the light includes an extreme ultraviolet ray.

14. The method of claim 12, wherein
  $R_1$ is hydrogen, $R_8CO^-$, or $R_9SO_2^-$,
  $R_2$ is $R_{10}CO^-$ or $R_{11}SO_2^-$,
  $R_3$, $R_4$, $R_5$, $R_6$, and $R_7$ are each hydrogen,
  $R_8$ and $R_9$ are each independently a halogen-substituted or halogen-unsubstituted C1 or C2 alkyl group or a halogen-substituted or halogen-unsubstituted C6 to C20 aryl group,
  $R_{10}$ is an unsubstituted C1 or C2 alkyl group or an unsubstituted C6 to C20 aryl group, and
  $R_{11}$ is a halogen-substituted or halogen-unsubstituted C1 or C2 alkyl group or a halogen-substituted or halogen-unsubstituted C6 to C20 aryl group.

15. The method of claim 14, wherein the hypervalent iodine compound includes a compound of Chemical Formula M2 or Chemical Formula M3,

[Chemical Formula M2]

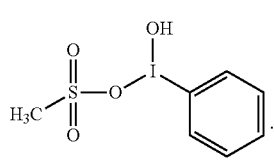

[Chemical Formula M3]

16. The method of claim 15, wherein the composition further includes a photo-acid generator,
  wherein the compound of Chemical Formula M2 and the compound of Chemical Formula M3 each have a lowest unoccupied molecular orbital (LUMO) energy level that is greater than that of the photo-acid generator.

17. The method of claim 12, wherein
  $R_1$ is $R_8CO^-$ or $R_9SO_2^-$, and
  $R_8$, $R_9$, $R_{10}$, and $R_{11}$ are each independently a halogen-substituted or halogen-unsubstituted C1 or C2 alkyl group or a halogen-substituted or halogen-unsubstituted C6 to C20 aryl group.

18. The method of claim 17, wherein the hypervalent iodine compound includes a compound of Chemical Formula M4 or Chemical Formula M5,
  wherein the hypervalent iodine compound has a lowest unoccupied molecular orbital (LUMO) energy level that is less than that of diphenyliodonium triflate and that of triphenylsulfonium triflate,

[Chemical Formula M4]

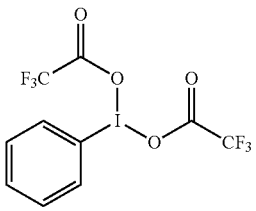

-continued

[Chemical Formula M5]

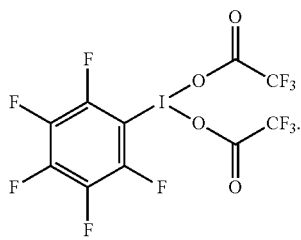

19. The resist composition of claim 1, wherein R20 and/or R21 is a substituted or unsubstituted C1 to C15 alkyl group.

20. The resist composition of claim 1, wherein the composition further includes a photo-acid generator,
the compound of Chemical Formula 1 has a lowest unoccupied molecular orbital (LUMO) energy level that is greater than that of the photo-acid generator, and
the photo-acid generator comprises

[Chemical Formula M4]

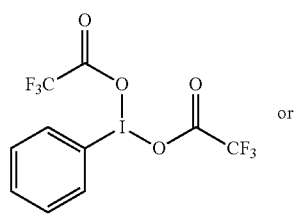

or

[Chemical Formula M5]

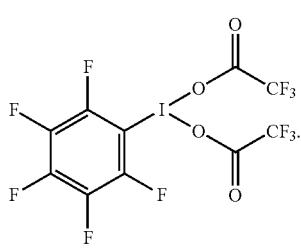

21. An extreme ultraviolet resist composition comprising a hypervalent iodine compound of Chemical Formula M3

[Chemical Formula M3]

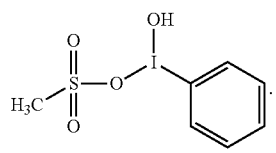

22. An extreme ultraviolet (EUV) resist composition comprising a hypervalent iodine compound of Chemical Formula 1,

[Chemical Formula 1]

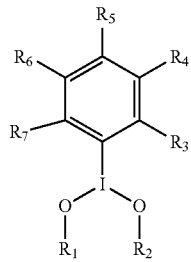

wherein:
R1 is hydrogen, —C(O)CH3, —C(O)CF3, or R9SO2-,
R2 is —C(O)CF3, —C(O)CH3, or R11SO2-,
R3, R4, R5, R6, and R7 are each independently a hydrogen, a halogen, a halogen-substituted C1 or C2 alkyl group, or a halogen-substituted C6 to C20 aryl group, and
R8, R9, R10, and R11 are each independently a substituted or unsubstituted C1 or C2 alkyl group or a substituted or unsubstituted C6 to C20 aryl group
wherein the resist composition further comprises:
a quencher; and
a polymer comprising a compound of Chemical Formula 2A or 2B:

[Chemical Formula 2A]

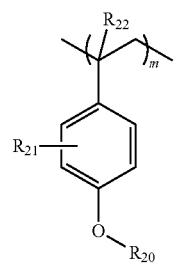

wherein R20, R21, and R22 are each independently hydrogen or a substituted or unsubstituted C1 to C15 alkyl group, and m is an integer between 10 and 1,000,000, or

[Chemical Formula 2B]

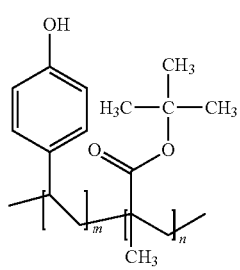

wherein m is an integer between 10 and 1,000, and n is an integer between 10 to 1,000, wherein the resist composition forms a layer when exposed to EUV light at a wavelength of about 10 nm to about 124 nm.

* * * * *